US005939256A

United States Patent [19]
Yamamoto et al.

[11] Patent Number: 5,939,256
[45] Date of Patent: Aug. 17, 1999

[54] DETECTION OF NUCLEIC ACID HYBRID VARIATION WHICH INTERACTS WITH DOUBLE HELIX OR WITH SECOND REAGENT THROUGH DOUBLE HELIX BY CHARGE TRANSFER AND PROBE FOR HYBRIDIZING WITH TARGET NUCLEIC ACID

[75] Inventors: Nobuko Yamamoto, Isehara; Tadashi Okamoto, Yokohama; Yoshinori Tomida; Masahiro Kawaguchi, both of Atsugi; Keisuke Makino; Akira Murakami, both of Kyoto, all of Japan

[73] Assignee: Canon Kabushiki Kaisha, Tokyo, Japan

[21] Appl. No.: 08/683,918

[22] Filed: Jul. 19, 1996

Related U.S. Application Data

[63] Continuation of application No. 08/157,318, Nov. 26, 1993, abandoned.

[30] Foreign Application Priority Data

Nov. 27, 1992 [JP] Japan .................................... 4-318959
Nov. 30, 1992 [JP] Japan .................................... 4-320500

[51] Int. Cl.⁶ ..................................................... C12Q 1/68
[52] U.S. Cl. ................................ 435/6; 436/501; 935/77; 935/78
[58] Field of Search ........................ 435/6, 810; 436/501; 536/22.1, 23.1, 24.8, 24.3–24.33, 25.3; 935/77, 78

[56] References Cited

U.S. PATENT DOCUMENTS

| | | | |
|---|---|---|---|
| 3,786,369 | 1/1974 | Drexhage et al. | 531/945 |
| 4,341,894 | 7/1982 | Regan et al. | 544/333 |
| 4,555,396 | 11/1985 | Frank et al. | 424/3 |
| 4,840,784 | 6/1989 | Frank et al. | 424/3 |
| 5,229,297 | 7/1993 | Schnipelsky et al. | 436/94 |
| 5,278,043 | 1/1994 | Bannwarth et al. | 536/23.1 |
| 5,324,829 | 6/1994 | Ball et al. | 536/23.1 |
| 5,591,578 | 1/1997 | Meade et al. | 435/6 |

FOREIGN PATENT DOCUMENTS

| | | |
|---|---|---|
| 0229943 | 7/1987 | European Pat. Off. . |
| 0232967 | 8/1987 | European Pat. Off. . |
| 320308 | 6/1989 | European Pat. Off. .......... C12Q 1/68 |
| 0439036 | 7/1991 | European Pat. Off. . |
| 455517 | 11/1991 | European Pat. Off. .......... C12Q 1/68 |
| 487218 | 5/1992 | European Pat. Off. .......... C12Q 1/68 |
| 0512334 | 11/1992 | European Pat. Off. . |
| 63-238166 | 10/1988 | Japan . |
| 1-153683 | 6/1989 | Japan . |
| 2-75958 | 3/1990 | Japan ............................ G01N 33/58 |
| 2-295496 | 12/1990 | Japan ............................ C12Q 1/68 |
| WO8603227 | 6/1986 | WIPO . |
| WO8910415 | 11/1989 | WIPO .............................. C12Q 1/68 |
| WO9310267 | 5/1993 | WIPO . |

OTHER PUBLICATIONS

Risser et al. "Electron Transfer in DNA: Predictions of Experimental Growth and Decay of Coupling with Donor–Acceptor Distance", J. Am. Chem. Soc., Jan. 1993, pp. 2508–2510.

Balaban et al., "Regioselective Deuteriation Kinetics . . . or 3–Phenyl Groups", J. Labelled Compounds and Radiopharmaceuticals, vol. XIX, No. 6, (1982) pp. 783–793.
Wizinger, et al. Helv. Chim. Acta, vol. 39, No. 2, Fas. I, pp. 5–15 (1956) Balban, et al., "Charge–Transfer . . . Iodides", Tetrahedron, vol. 20, pp. 119–130 (1963).
Detty, et al., "Chalcogenapyrylium . . . Oxidase", J. Med. Chem. vol. 33, pp. 1108–1116, (1990).
Sanford, et al., "The Growth . . . Cells", J. Nat'l. Cancer Inst., vol. 9, No. 3, pp. 229–246 (1948).
Kasai et al., "Photosensitized Formation . . . Mediated Reaction", J.A.C.S., vol. 114, pp. 9692–9694, 1992.
Arnold et al., "Assay Formats . . . DNA Probes", Clinical Chem. vol. 35, No. 8, p. 1588–1594 (1989).
Murakami et al., "Structural Analysis . . . Oligonucleotides", Nucleic Acids, Symposium Series, vol. 22, pp. 27–28 (1990).
Ito et al., "8–Hydroxydeoxyguanosine . . . ", J. Biol. Chem., vol. 268, No. 18, pp. 13221–13227 (1993).
Morrison et al., "Solution Phase Detection of Polynucleotides Using Interacting Fluorescent Labels and Competitive Hybridization", Analytical Biochem., 183, 231–244 (1989).
C. Picard et al., "Detection and Enumeration of Bacteria in Soil by Direct DNA Extraction and Polymerase Chain Reaction", Appl. and Env. Microbio., 58, 9, 2717–22 (1992).
D. Basting et al., "New Laser Dyes", Appl. Phys., 3, 81–88 (1974).
G. Hauke et al., "Absorption and Fluorescence of Pyrylium Salts", Ber. Bunsenges. Phys. Chem., 96, 7, 880–86 (1992).
O. Strobel et al., "Preparation and Characterization of Spin–Labeled Oligonucleotides for DNA Hybridization", Bioconjugate Chem., 1991, 2, 89–95 (1991).
A. Rahman et al., "Complexes involving quercetin, DNA and Cu(II)", Carcinogenesis, 11, 11, 2001–03 (1990).
Lett et al., "New Fluorochromes, Compatible with Hgh Wavelength Excitation, for Flow Cytometric Analysis of Cellular Nucleic Acids", Cytometry, 5, 339–47 (1984).
P. Cullis et al., "Electron Conduction and Trapping in DNA—An Electron Spin Resonance Study", J. Chem. Soc.—Faraday Trans., 86(3), 591–92 (1990).

(List continued on next page.)

Primary Examiner—Ardin H. Marschel
Attorney, Agent, or Firm—Fitzpatrick, Cella, Harper & Scinto

[57] ABSTRACT

A method for detecting a nucleic acid hybrid comprises steps of adding a nucleic acid probe into a sample solution containing a targeted nucleic acid, and detecting a double helical structure of a hybrid formed between the probe and the targeted nucleic acid, wherein the step for detecting the double helical structure comprises incorporating, into the sample solution, two or more kinds of reagents which are capable of causing a detectable change by interaction therebetween through the double helical structure and measuring the change caused by the interaction of the reagents; and at least one of the two or more kinds of reagents is joined to the probe.

47 Claims, 4 Drawing Sheets

OTHER PUBLICATIONS

M. Detty, "Rational design of properties in chalcogenapyrylium dyes", *New Directions in Photodynamic Therapy*, Proceedings of SPIE—The International Society for Optical Engineering, 847, 68–73 (1987).

N. Yamamoto et al., "Novel Intercalators of Pyridium Dye Into Double–Stranded DNA", *Nucl. Acids Symp. Ser.*, 29, 83–84 (1993).

M. Purugganan et al., "Accelerated Electron Transfer Between Metal Complexes Mediated by DNA", *Science*, 241, Sep. 23, 1988, 1645–49.

Shimidzu, et al., "Synthesis . . . "Nucleic Acids Symp. Ser. vol. 27, pp. 97, 98, Nov. 1992.

Fromherz, et al., "Photoinduced . . . "JACS, vol. 108, pp. 5351–5862, 1986.

Baron, et al., "DNA–mediated . . . " JACS, vol. 108, pp. 6391–6393, 1986.

Smits et al., "Relationship Between Solvation as Expressed . . . " Anal. Chem., vol. 45, No. 2, Feb. 1973, pp. 339–342.

Brun et al., "Dynamics of Electron Transfer Between . . . " J.A.C.S., vol. 114, No. 10, pp. 3656–3660, 1992.

Matthew et al. (1988) Analytical Biochemistry, vol. 169, pp. 1–25.

Cardullo et al. (1988) Proc. Natl Acad Sci (USA), vol. 85, pp. 8790–8794.

Murphy et al. (1993) Science, vol. 262, pp. 1025–1029.

"A DNA Probe of Ruthenium bipyridine Complex Using Photocatalytic Activity", Chemistry Letters, pp. 1889–1892 (1989), Kojima et al.

J.Am.Chem.Soc.1989, 111, pp. 7721–7726, Telser et al.

J.Am.Chem.Soc.1989, 111, pp. 7226–7232, Telser et al.

J.Am.Chem.Soc.1990, 112, pp. 4960–4962, Friedman et al.

J.Am.Chem.Soc.1992, 114, pp. 8736–8738, Jenkins et al.

"Photoelectro Transfer Between Molecules Adsorbed in Restricted Spaces", Photochem. Convers, etc., Turro N. et al., 1990, pp. 123–139.

J. Photochem. Photobiol. 1988, 47, 85S, Helene C. et al.

Nucleic Acids Res. 1987, 15, 8643–8659, T.L. Doan et al.

DETECTION OF NUCLEIC ACID HYBRID VARIATION WHICH INTERACTS WITH DOUBLE HELIX OR WITH SECOND REAGENT THROUGH DOUBLE HELIX BY CHARGE TRANSFER AND PROBE FOR HYBRIDIZING WITH TARGET NUCLEIC ACID

This application is a continuation of application Ser. No. 08/157,318 filed Nov. 26, 1993, now abandoned.

BACKGROUND OF THE INVENTION

1. Field of the Invention

The present invention relates to a method for detecting and identifying a desired specific base sequence in a nucleic acid (DNA or RNA) of viruses, animals, plants, and human beings, or detecting mutation in a base sequence. The present invention also relates to a probe for the above method.

2. Related Background Art

As the result of progress of nucleic acid analysis technique, a number of mutant genes have been found, and a variety of genetic diseases caused by a mutant gene are being elucidated. Some of the genetic diseases have been found to be caused by local deficiency of a base, or point mutation of a base in a gene. The abnormality in the gene gives rise to mutation of protein to show various symptoms. At present, such genetic diseases are diagnosed mainly after manifestation of the symptom by enzymatic assay or by an immunological method employing an antibody. However, from the standpoint of early therapy, it is considered to be important to find mutation of the gene before manifestation of a serious symptom.

One of effective methods for the diagnosis is RFLP (restriction fragment length polymorphism). In this method, for example, the whole gene of a human being is cut by restriction enzymes, and the resulting DNA fragment is developed by agarose gel electrophoresis, fixed on a filter by a Southern blotting method, and hybridized with a probe comprising a DNA (or RNA) labeled by an isotope or the like. From the difference of the cut pattern of the DNA of the sample from that of a normal DNA, the gene is detected which causes the disease.

The DNA diagnosis is useful not only for genes of human being but also for identification of infecting bacteria.

Hitherto, the kind of an isolated bacterium is identified by similarity in morphological properties and biochemical properties thereof. This method has disadvantages in that incubation of the bacterium requires a long time, judgment of the properties depends on the method of testing, the identification result differs depending on the selection of properties to be tested, and so forth.

In recent years, DNA-DNA hybridization or DNA-RNA hybridization has been tried particularly in detection and identification of microbism-causing bacteria. In this method, nucleic acid (DNA or RNA) is extracted from a bacteria, and a specified portion of nucleic acid of the bacteria which has a base sequence having homology to the tested nucleic acid sample is detected by hybridization, whereby the presence of the targeted bacteria in the sample is judged.

The hybridization, which is a basic technique for the above test, generally comprises the steps below.
(1) Cutting of DNA into fragments, and development thereof by gel-electrophoresis;
(2) Adsorption of the developed respective DNA fragments on a nitrocellulose filter (Southern blotting);
(3) Formation of a hybrid by reaction of the DNA fragment on the nitrocellulose filter in the step (2) above with a probe; and
(4) Detection of the DNA fragment which has formed a hybrid.

In hybridization between DNAs, a labeled probe DNA and a targeted DNA form a hybrid between the respective complementary portions by hydrogen bonding.

The probes employed in the hybridization reaction are changing with the times. In the earliest stage of the research, a long DNA fragment was labeled with an radioactive isotope by nick translation. With the development of a DNA synthesizer, a synthesized oligonucleotide has been used in place of a long DNA, and the labeling substance has been changed from a dangerous radioactive isotope to a safe biotin-avidin type reagent, and further to a chemiluminescence type reagent.

For precise hybridization between complementary sequences, the reaction temperature and the ion strength should be selected to be optimum. At a higher temperature, the probe does not combine with the nucleic acid having a complementary sequence. At a lower temperature, the probe combines non-specifically with the nucleic acid. For higher preciseness, it is necessary to eliminate instable hydrogen bonding by lowering the salt concentration of the solution or raising the temperature of the solution and to wash away non-specifically combined probes or mismatched probes. Accordingly, many trial-and-error experiments are required to select the optimum conditions for the reaction and the washing.

In genetic diagnosis, for higher precision, the conditions for the hybridization reaction and the washing should be decided strictly such that mismatch of one base pair level is eliminated.

In a hybridization reaction, immobilization of a targeted nucleic acid on a support like nitrocellulose has the advantage of ease in washing for elimination of non-specific bonding, etc. of the probe, but has disadvantages in complexity of operation, difficulty in automation of the test, and an extended time required for operation. Therefore, this method is not suitable for treatment of a large number of samples.

If a method is found for detecting a hybrid in a solution without immobilization of nucleic acid, it enables automation of the detection. Many attempts are being made therefor. The most important problem in eliminating the nucleic acid immobilization step is how to differentiate the probe combined with the targeted nucleic acid from excess non-combined probe (namely B/F separation). In this method also, selection of the reaction conditions and the washing conditions is important similarly as in the aforementioned hybridization employing immobilized nucleic acid to avoid non-specific adsorption and mismatch of probes.

To detect a hybrid of targeted nucleic acid with a probe without B/F separation, several methods are disclosed which employ fluorescence depolarization (see Japanese Patent Application Laid-Open Nos. 2-295496 and 2-75958). In these methods, a fluorescence-labeled single-stranded DNA probe is brought into contact with a DNA in a sample to form a double-stranded DNA, and the change of the fluorescent polarization by the double strand formation is measured. Thereby the presence of a base sequence in the DNA in the sample corresponding that of the probe is detected. Such a method is grounded on the principle that a fluorescent substance bonded to the single strand is made less movable by formation of a double strand to increase its fluorescence anisotropy.

In these methods, however, a complicated preliminary operation is necessary to remove completely any contaminant such as protein from the sample, since a contaminant in the sample will be adsorbed non-specifically by the probe DNA to increase background in hybrid detection. Further, non-specifically adsorbed probe DNA and a pseudo-hybrid formed by mismatch with a base need to be removed similarly as in detection in other solution systems. In these methods, although B/F separation is not necessary, the probe concentration should be at the same level as that of the targeted DNA in measurement of the change of fluorescent polarization.

As described above, the detection of a targeted nucleic acid by hybridization reaction, when the B/F separation is required for the detection, is troublesome because of a number of operations such as B/F separation (removal of excess probe), removal of non-specifically adsorbed matter and mismatching probes, and so forth, whether the targeted nucleic acid is immobilized or not. Furthermore, the optimum conditions of the respective operations vary depending on the probe length, and the respective base sequences, so that the operating conditions have to be set for each of the cases. In particular, the location of mismatched base on the probe affects significantly the stability of the hybrid, and in some cases the mismatched hybrid is not removable owing to the location of the mismatching base. Therefore, the conditions for hybridization reaction have to be decided in consideration of the liability of mismatching of the base, which requires further troublesome operations.

The detection methods by measurement of change of fluorescence without B/F separation also require complicated treatment for preventing non-specific adsorption and mismatching, or for removing non-specifically adsorbed matters or mismatched matters. Moreover, a contaminant may impair the sensitivity of the measurement, and the probe concentration needs to be at the same level as the targeted nucleic acid. Therefore, these methods require use of a sufficient amount of a sample, and cannot be applied to microanalysis, disadvantageously.

The present invention has been made to cancel the aforementioned disadvantages of prior art.

SUMMARY OF THE INVENTION

An object of the present invention is to provide a method of detection of a targeted nucleic acid by utilizing hybridization by simpler steps without B/F separation at high measurement sensitivity, and to provide a probe therefor.

Another object of the present invention is to provide a method of detection of a targeted nucleic acid which enables precise detection of only a desired hybrid even in the presence of a mismatched hybrid, and to provide a probe therefor.

According to an aspect of the present invention, there is provided a method for detecting a nucleic acid hybrid comprising the steps adding a nucleic acid probe into a sample solution containing a targeted nucleic acid, and detecting a double helical structure of a hybrid formed between the probe and the targeted nucleic acid, the step for detecting the double helical structure comprising incorporating, into the sample solution, two or more reagents which are capable of causing a detectable change by interaction therebetween through the double helical structure, and measuring the change caused by the interaction of the reagents; and at least one of said two or more kinds of reagents being joined to the probe.

According to another aspect of the present invention, there is provided a method for detecting a nucleic acid hybrid comprising the steps adding a nucleic acid probe into a sample solution containing a targeted nucleic acid, and detecting a double helical structure of a hybrid formed between the probe and the targeted nucleic acid, the step for detecting the double helical structure comprising incorporating, into the sample solution, a reagent which is capable of causing a detectable change by interaction with the double helical structure, measuring the change caused by the interaction of the reagent with the double helical structure.

According to still another aspect of the present invention, there is provided a probe for detection of a targeted nucleic acid, having a sequence for hybridization with the targeted nucleic acid: the probe being linked to at least one of two or more reagents which are capable of causing detectable change by interaction between the reagents through a double helical structure formed by hybridization of the targeted nucleic acid and the probe.

According to a further aspect of the present invention, there is provided a probe for detection of a nucleic acid hybrid, having a sequence for hybridization with the targeted nucleic acid: the probe being linked to a reagent which is capable of causing detectable change by interaction with a double helical structure formed by hybridization of the targeted nucleic acid with the probe.

According to a still further aspect of the present invention, there is provided a method of detection of a targeted nucleic acid, comprising adding a probe having at least two pigments linked thereto into a sample solution, detecting a double helical structure of a hybrid formed between the probe and the targeted nucleic acid in the sample solution by optical change given by charge-transfer between the pigments through the double helical structure.

According to still further aspect of the present invention, there is provided a probe for detection of a targeted nucleic acid, having a sequence for hybridization with the targeted nucleic acid: the probe being linked to two or more pigments which are capable of causing detectable optical change by charge transfer therebetween through a double helical structure formed by hybridization of the targeted nucleic acid and the probe.

DESCRIPTION OF THE PREFERRED EMBODIMENTS

Figure 1A:
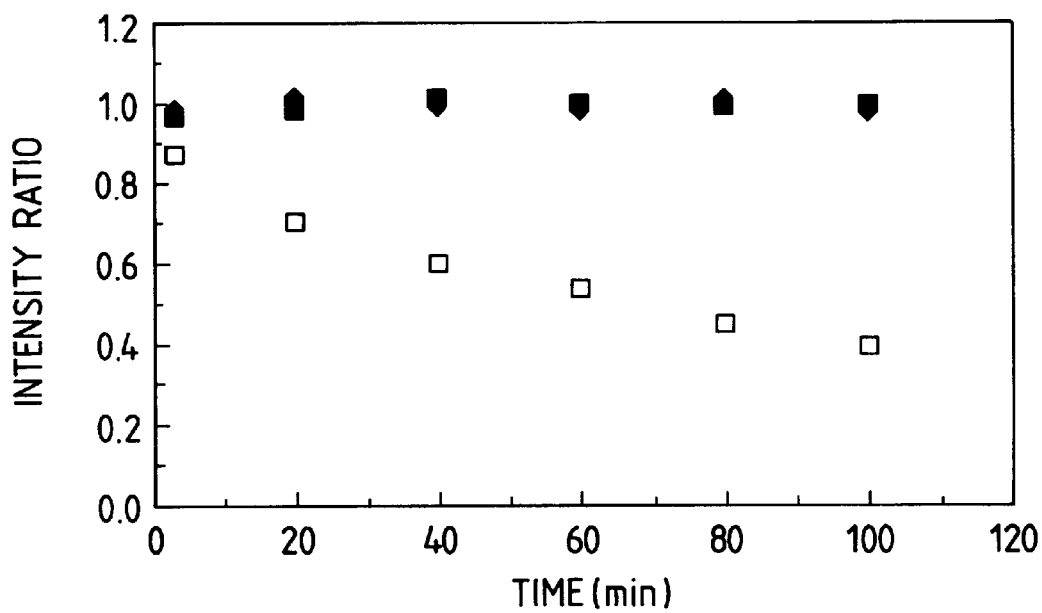
FIG. 1A is a graph showing change of the signal intensity ratio with lapse of time in Example 1.

The present invention provides a method of detection of a hybrid grounded on a novel principle different from that of the prior art. The method of the present invention detects formation of a double helical structure resulting from hybrid formation without a B/F separation step. Further, the present invention enables detection of only a desired normal double helical structure with improved accuracy, even when non-specific adsorption or mismatching occurs, by selecting the conditions for detection only of a normal double helical structure without any additional treatment. The present invention is applicable to the cases where the nucleic acid forms a regular double helix such as the cases of DNA-DNA hybridization, and DNA-RNA hybridization.

The present invention is described below in detail.

The phenomenon of hybridization has been understood only from the viewpoint of hydrogen bonding between complementary nucleic acid bases. Therefore, hybridization reaction has generally been conducted after immobilizing the nucleic acid (DNA or RNA). On the contrary, in hybridization in a solution, when a nucleic acid forms a double strand of a certain length, the double strand is expected to form a double helical structure. The inventors of the present invention noticed the differences of a single-stranded nucleic acid from a double-stranded nucleic acid (hybrid) in the higher order structures and chemical properties, and established a detection system, whereby the present invention has been completed.

In the double helical structure, the nucleic acid base portions form a base pair by hydrogen bonding with the phosphoric acid portions and the sugar portions directing outside. The nucleic acid bases are stabilized by mutual stacking and take position at the center of the helix axis. The double helical structure includes an A form, a B form, a C form, a Z form, and variations thereof, which differ not only in the base sequence but in pitch length, symmetry of the helix, the width of the groove, the depth of the groove, etc. depending on the ion species, the salt concentration, etc. in annealing. Even with the same sequence, the double helical structure is said to vary depending on the conditions. In general, DNA is said to be in a B form structure, in which the pitch is 33.8 Å and the number of nucleic acid base is ten bases per pitch.

The present invention relates to a method for detection of formation of a double helical structure by measuring a chemical change of an added reagent which causes a detectable change through a double helical structure of a hybrid.

The useful reagents include two types:

(a) the one which causes a detectable change by reaction (or interaction) with the double helix itself, and (b) combination of two or more reagents which interact in the presence of a double helical structure, thereby causing a detectable change.

Firstly, the method which employs the reagent of type (a) above is explained.

In the case where the reagent of type (a) is used, a probe having the reagent linked thereto is reacted with a sample solution to form a hybrid of the probe and a targeted nucleic acid, and the double helical structure of the hybrid is detected by the change of the constituents of the nucleic acid. The change caused by reaction of the reagent bonded to the probe with the double helical structure may be detected by direct measurement of the above change of the reagent if this change is measurable by itself, or otherwise by inducing another change which makes the change of the reagent detectable and by measuring the resulting detectable change. Further, the change of the constituent of the nucleic acid is detected by decomposition into nucleic acid and nucleotide and analyzing directly by HPLC, or by use of an antigen to the changed nucleoside.

The reagent which interacts with the double helical structure includes those which react with nucleic acid, etc. constituting the double helical structure to change by itself; those which cause a chemical or structural change in the double helix; and those which cause a detectable change by reacting with a third substance added in the reaction system in the presence of the double helical structure.

Such interaction which includes charge transfer between the double helical structure and the reagent may be used. In the charge transfer as the interaction, the reagent is employed which functions as an electron donor or an electron acceptor. The interaction is detectable, for example, as a change caused by the hybrid formation in the chemical structure of the reagent, double helix, or a third substance capable of interaction with the above substance, as a change of electronic state, or as the change in signal given by the changed substance.

The interaction grounded on the electron transfer includes the cases of "through-space" and "through-bond" similarly as in the (b) type reagent shown later. The examples are charge transfer through the stack of the nucleic acid base pairs and charge transfer caused by proximity effect between the electron donor and the electron acceptor resulting from the change of the structure to double helix.

In the cases where charge transfer is less likely to occur between the double helical structure and the reagent, a mediator for the charge transfer, or a sensitizer may be used.

The change of the interaction between the double helical structure and the reagent may be detected by measuring the change of the electron acceptor. This method is classified according to the detection means.

For example, the transferred charge is detected, by use of a spin-labeling agent, as spectrum change in ESR by spin elimination or the like method, or detected by emergence of a new absorption spectrum like a charge transfer absorption band or a change of absorption spectrum. In the system in which the charge transfer causes coloration or discoloration of the solution, the change can be confirmed visually: this system is useful as a simplified system. A light-emitting system like fluorescence and phosphorescence is also useful for the reaction in which the fluorescence or the phosphorescence arises or disappears as the result of the interaction. An electron acceptor which changes chemically into another substance by the charge transfer may be used for the detection of the charge transfer, where the substance formed by the change may be detected by adding a third substance to the system to cause chemiluminescence. In this detection, if the third substance is an enzyme or an antigen, it may be detected by bioluminescence.

The interaction may be detected by the change of an electron donor instead of the aforementioned change of an electron acceptor. In such methods of detection, most of the detecting techniques as described for the electron acceptor are applicable without modification. If the electron donor is a fluorescent substance, a change like fluorescence quenching may be directly detected by decrease of quantum yield of the fluorescence as the consequence of charge transfer, or otherwise the resulting change may be made visible by an additional reaction.

If the reagent is an electron donor to the double helical structure, a third substance may be added which stimulates the reagent electron donor to generate electrons provided that the third substance does not be activated to emit electron to cause charge transfer.

If the reagent is an electron acceptor to the double helical structure, it may be activated and thereby electrons are drawn out from the electron acceptor, where the activation may be caused by light or another initiating agent like in the case of the electron donor.

A mediator for mediating the charge transfer or a sensitizer may be present as a third substance as mentioned before. Such a substance may interact with the double helix to promote charge transfer to the electron donor or the electron acceptor which is not directly bonded to the double helix.

The reagent of type (a) which combines with the probe may be any substance which has an oxidation-reduction potential similar to the oxidation-reduction potential of the nucleic acid. Examples thereof include reagents capable of withdrawing electrons such as riboflavin; oxidizing agents such as N,N'-dimethyl-2,7-diazapyrenium ion; basic dyes such as xanthene dyes, e.g., Rose Bengale, Floxin B, eosin, etc. and azine dyes, e.g., methylene blue, Safranine T, etc. The reagent may be any substance which causes a detectable change in the reagent itself or the nucleic acid.

Next, the method which employs the aforementioned reagent of type (b) is explained.

In this method, a hybrid is detected by measuring a change given by interaction between the two or more reagents caused by the structural change of nucleic acid from a single strand form to a double strand form. The interaction herein includes charge transfer. When the interaction is charge transfer, the "two or more reagents" comprise at least one combination of an electron donor and an electron acceptor, and occurrence of the interaction is detected, for example, as a change of the chemical structure, a change of the electronic state, or a change of a signal of the changed substance which is brought about by the hybrid formation.

The relation between the electron donor and the electron acceptor depends on the energy states of the both substances. In the present invention, the electron donor or the electron acceptor is not necessarily used as generally defined. In the combination of two or more reagents, the electron donor and the electron acceptor are suitably selected. As well known, for example, anthracene is classified as a typical electron donor according its oxidation-reduction potential, but simultaneously has characteristics of an electron acceptor.

The interaction of the electron donor and the electron acceptor includes the cases of "through-space" and "through-bond". The through-space cases include interaction through the stack of nucleic acid base pairs and interaction caused by proximity effect between the electron donor and the electron acceptor resulting from the change of the structure to a double helix. The through-bond cases include transfer of electric charge through bases, phosphoric acid moieties, and sugar moieties constituting the nucleic acid. In any case, the type of the interaction is not limited provided that the interaction is caused by the double helix formation.

The interaction through the stack of nucleic acid base pairs is a phenomenon that electrons released from an electron donor are transferred by an electron cloud spreading over the nucleic acid base pairs through the adjacent nucleic acid pairs successively to an electron acceptor when the distance between the electron donor and the electron acceptor is so large that the interaction cannot be caused primarily, or conversely a phenomenon that an electron acceptor withdrawns electrons from a nucleic acid base pair and electrons are withdraw successively, finally from an electron donor. In short, the nucleic acid base pairs function as a mediator in charge transfer.

On the other hand, the interaction caused by proximity effect between the electron donor and the electron acceptor occurs when formation of double helical structure brings an electron donor and an electron acceptor close to each other to enable interaction. For example, an electron donor and an electron acceptor are both bonded to a probe at such a distance that the interaction does not occur when the probe is in a single-stranded state and that the interaction occurs when the probe hybridizes with a targeted nucleic acid into a double helical structure. Thereby, the formation of a double helical structure can be detected by detecting the occurrence of the interaction. If the charge transfer does not occur readily through the double helical structure between the electron donor and the electron acceptor, a mediator which mediates the charge transfer, or a sensitizer may naturally be added.

The electron donor and the electron acceptor are required to be positioned at such sites that the donor and the acceptor are capable of reacting with the double helical structure to cause the interaction as described above in the present invention. The reagent is positioned so as to be capable of reacting with the double helical structure by insertion between a nucleic acid base pair like an intercalator, by embedding in a groove of the double helical structure, by placing close to the double helical structure, or by a like method. In any case, the reagent is required essentially in the present invention to be positioned to be specific to the double helical structure of a hybrid formed from a single-stranded probe and a targeted nucleic acid.

Of the methods of positioning of the reagent, the use of intercalator is most profitable in charge transfer through stacked base pairs. The intercalator is generally a planar compound having a spread of electron cloud. The intercalator is placed and oriented in a direction parallel to the nucleic acid base pairs between the base pairs at the same distance as that between the base pairs. For example, when an intercalator is used as the electron donor and an electron acceptor is placed at the opposite side of the double helix, an electron released from the electron donor can be sent to the adjacent nucleic acid base pair, and further through the electron cloud of the nucleic acid base pairs toward the electron acceptor. Conversely, when an intercalator is used as the electron acceptor and an electron donor is placed at the opposite side of the double helix, an electron can be withdrawn by an electron hole of the electron acceptor from an adjacent nucleic acid pair, and further electrons are pulled out successively between the nucleic acid bases, and finally from the electron donor, thus causing charge transfer. Considering the above matters, in charge transfer through stacked base pairs, at least one of the electron donor and the electron acceptor is preferably an intercalator. More preferably both of them are respectively intercalators for improving the charge transfer efficiency. Furthermore, the intercalator is known to stabilize the double helical structure and to raise the melting temperature thereof. Therefore, use of an intercalator as the electron donor or the electron acceptor is advantageous in stabilizing the hybrid of the probe and the targeted nucleic acid.

The change of the interaction between two or more reagents resulting from double helix formation can be detected by change of the electron acceptor. This method is classified according to the detection means.

For example, the transferred charge is detected, by use of a spin-labeling agent, as spectrum change in ESR by spin elimination or the like method, or detected by emergence of a new absorption spectrum like a charge transfer absorption band or a change of absorption spectrum. In the system in which the charge transfer causes coloration or discoloration of the solution, the change can be confirmed visually: this system is useful as a simplified system. A light-emitting system like fluorescence and phosphorescence is also useful for the reaction in which the fluorescence or the phosphorescence arises or disappears as the result of the interaction. An electron acceptor which changes chemically into another substance by the charge transfer may be used for the detection of the charge transfer, where the substance formed by the change may be detected by addition of a third substance to the system to cause chemiluminescence by the reaction of the two substances. In this detection, if the third substance is an enzyme or an antigen, it may be detected by bioluminescence.

In another method, the interaction may be detected by the change of an electron donor instead of the aforementioned change of an electron acceptor. In this method of detection, most of the detecting techniques as described for the electron acceptor is applicable with little modification. If the electron donor is a fluorescent substance, the change like fluorescence quenching may be directly detected by decrease of quantum yield of the fluorescence as the consequence of charge transfer, or the resulting change may be made visible by an additional reaction.

In addition to the electron donor and the electron acceptor, a third substance may exist which stimulates the reagent electron donor to generate an electron except in the cases where the electron acceptor is activated by light or the like to release an electron and initiate charge transfer.

The electron acceptor may be activated and thereby electron is withdrawn from the electron acceptor, where the activation may be caused by light or another initiating agent like in the case of the electron donor.

A mediator for the charge transfer, or a sensitizer may be present as a third substance as mentioned before. Such a substance may interact with the double helix to promote charge transfer to the electron donor or the electron acceptor which is not directly bonded to the double helix.

The electron donor and the electron acceptor, used in the present invention, if the both are in free states in the reaction system, may possibly interact with each other irrespectively of the presence or absence of the double helical structure, which will increase background of the measurement to lower S/N ratio. Therefore, at least one of them is desirably linked to the probe preliminarily for precise detection. The linking of the electron donor or the electron acceptor to the probe is made through a linker such as —$(CH_2)_n$—, if necessary. The linking site is selected so as to achieve the interaction most efficiently.

The most desirable is the case where both of the electron donor and the electron acceptor are linked to the probe. In such a case, respective sites of the interacting reagents are known, so that the interaction can be controlled by selecting the sites on the probe, advantageously. The spatial interval between the electron donor and the electron acceptor on the probe is selected suitably depending on the kinds thereof. For example, for utilizing proximity effect, the interval is preferably in the range of from 20 to 120 Å more preferably from 50 to 80 Å in the formed hybrid, namely in the double helical structure. For utilizing charge transfer through the double helical structure, the interval is decided in consideration of change of the DNA structure such as unwinding caused by the respective dyes, and is preferably in the range of from 20 to 120 Å. The preferred interval differs depending on whether the electron donor and the electron acceptor are both an intercalator or one or both of them are inserted to the primary groove or the secondary groove. Therefore, the interval is not limited to be in the aforementioned range. If the interval is too short, the charge transfer between the donor and the acceptor occurs directly without the interaction of the nucleic acid. Therefore, the interval is more preferably in the range of from 50 to 80 Å. The donor and the acceptor are preferably linked separately at the respective ends of the probe from the ease of linking although it depends on the length of the probe.

The length of the probe is selected suitably in an individual case so as to be capable of satisfactory hybridization with a targeted nucleic acid and of forming a stable double helical structure. In the case where both the electron donor and the electron acceptor are linked to the probe and the donor and the acceptor will interact each other in the absence of a double helical structure, the length of the probe is decided in consideration of the interval of the linked donor and acceptor so that the interval is sufficient to prevent the interaction. The length is usually 8 bases or more, preferably 12 bases or more.

However, stability of the double helical structure is affected greatly not only by the probe length but by the base sequence itself, and salt concentration and ionic strength of the reaction system. A sequence having more G-C base pairs will form a more stable double helical structure since the G-C base pair has more hydrogen bonding than A-T base pairs. The increase of a KCl molar concentration from 0.01 M to 1 M is said to raise the melting point of DNA by 30° C. Further, existence of an intercalator contributes significantly to stability. Accordingly, a probe of a length of less than 8 bases may possibly be made useful by suitably selecting such stabilization factors.

In the embodiment of the present invention where only one of the electron donor and the electron acceptor is linked to the probe, two cases are included: (a) the other donor or acceptor is present in the reaction system during formation of the double helical structure by hybridization of the probe and the targeted nucleic acid and the interaction is allowed to proceed after the double helix formation; and (b) the other donor or acceptor is added to the reaction system after the double helix formation by hybridization to cause the interaction. In the embodiment where the both of the donor and the acceptor are linked to the probe, both are present in the reaction system during hybridization, and the interaction is caused after the double helix formation.

In the case (b) shown above, the specific examples of the reagents include spin-labeling agents such as 4,4-dimethyloxazolidine-N-oxyl (DOXXL) and its derivatives, 2,2,5,5-tetramethylpyrrolidine-N-oxyl (PROXL), and 2,2,6,6-tetramethylpiperidine-N-oxyl (TEMPO) and its derivatives; fluorescent intercalators such as acridine, anthracene, pyrene, ethidium bromide, pyrylium, proflavine, porphyrin, thiazole orange dimer (TOTO), oxazole yellow (YOYO), 4',6-diamino-2-phenylindole dihydrochloride (DAPI), propidium iodide (PI), and the like and their derivatives; fluorescent pigments such as cyanine, azulene, three-nucleus pigment, dansyl, fluorescein, eosin, rhodamine, riboflavine, and their derivatives; and the like. These compounds are used suitably as an electron donor, an electron acceptor, or a mediator according to their oxidation-reduction potential. Of the reagents, the intercalator is particularly preferred from the reasons described above.

A paper is found in J. Am. Chem. Soc. 1992, 114, 3656–3660 which reports that charge transfer occurs between two kinds of intercalators as pigments through the aid of DNA when the intercalators are added in free state to a double-stranded DNA, but does not suggest at all the application of the interaction to specific detection of DNA hybridization. In the method of this report, the two kinds of pigments are added in free state to the double-stranded DNA. Therefore this method cannot be applied to the present invention because the two kinds of dyes as intercalators interact with each other in addition to the interaction caused by the charge transfer through DNA, which increases background of measurement to make sensitive precise detection impossible.

EXAMPLE 1

[1] Preparation of 20-meric oligonucleotide probe linked with TEMPO (4-hydroxy-2,2,6,6-tetramethylpiperidine) as a spin-labeling agent (1) Synthesis of 4-aminohexylamino-2,2,6,6-tetramethyl-piperidine-N-oxyl (4-aminohexylamino-TEMPO)

In 30 ml of methanol, were dissolved 0.5 mmol of 4-oxo-TEMPO and 5 mmol of hexamethylenediamine dihydrochloride. Thereto, 0.4 mmol of sodium cyanoborohydride, and Molecular Sieve 3A were added. The mixture was stirred at room temperature for 24 hours to allow the reaction to proceed. The reaction solution was filtered through a glass filter to remove the Molecular Sieve, and the solvent was evaporated off from the filtrate under a reduced pressure. The resulting residue was dissolved in 30 ml of 1N hydrochloric acid, and the solution was extracted with chloroform. The chloroform phase was washed with water and then the chloroform was distilled off under a reduced pressure. Water was added to the residue, and water-insoluble matter was removed by filtration. The water was removed from the filtrate by distillation under reduced pressure. Thus, red oily matter was obtained.

(2) Synthesis of oligonucleotide

A 20-mer oligonucleotide having a base sequence partially complementary to a targeted DNA, M13mp18DNA (single strand), was synthesized by means of an automatic DNA synthesis apparatus (Model 381A, made by ABI Co.). The 5'-terminal dimethoxytrityl group was eliminated on the automatic synthesizing apparatus. The base sequence SEQ ID NO:1, was as below:

5'-GTTGTAAAACGACGGCCAGT-3'

(3) Synthesis of spin-labeled oligonucleotide probe

The nucleotide (1 μmol) synthesized in the above step (2) together with the CGP support thereof was transferred into a gastight syringe. The subsequent reaction was allowed to proceed in this syringe. Onto the CPG support, was added a solution of 50 mg of carbonyl-N,N'-diimidazole (CDI) in 1 ml of dioxane. It was left standing at room temperature for one hour. After washing with dioxane, 0.4 ml of 0.2M 4-aminohexylamino-TEMPO solution in DMSO was added thereto. It was left standing at 55° C. for 24 hours, and then washed successively with DMSO, dioxane, and methanol, and dried under a reduced pressure.

The spin-labeled oligonucleotide was separated by aqueous concentrated ammonia, deprotected in a conventional manner, and purified by RPLC in a conventional manner.

[2] Hybrid formation of TEMPO probe with M13mp18 DNA 0.2 μM of the oligonucleotide probe, prepared in the above process [1] having TEMPO introduced thereto, and 0.2 μM of M13mp18DNA (made by Takara Shuzo Co, Ltd.) were heated to 80° C. in 1 mM phosphate buffer solution/ 145 mM NaCl/5 mM KCl and gradually cooled to room temperature. Thereby, a probe-targeted DNA hybrid was prepared. To the reaction solution, fluorescein (made by Kodak Co.) was added to a final concentration of 10 μM. The resulting solution was subjected to ESR spectrum measurement as described below. Separately, the same operation was conducted without using M13mp18DNA to obtain a sample (probe alone).

[3] Measurement of ESR spectrum

In the ESR measurement, one sample was swept at interval of 20 minutes for 100 minutes, and the change with time of the intensity ratio and absorption line width was measured. The ESR apparatus used was made by JEOL Ltd. and the cell was an artificial quartz flat cell. The conditions of ESR and light irradiation were as below:

ESR

Frequency: 9.42 GHz

Modulation: 100 kHz, 0.1 mT

Field: 335 mT

Time constant: 0.3 sec

Power: 10 mW

Sweep time: 8 min

Receiver gain: 1.25×1000

Light irradiation

Monochrometer: 490 nm

Power supply: 88.5 V–89 V/22A

Figure 1B:
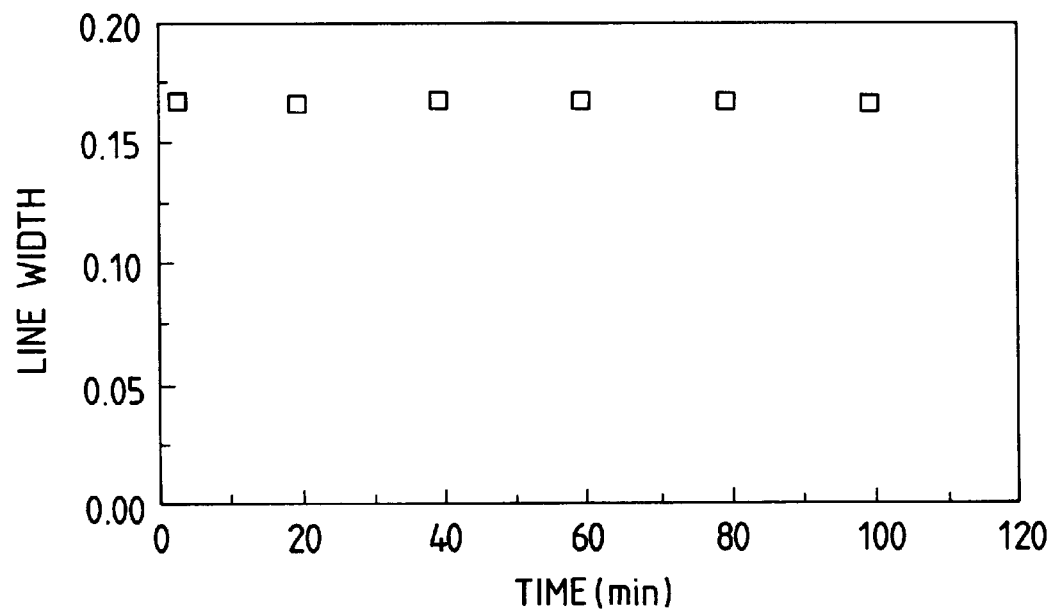
FIG. 1B is a graph showing change of the ESR signal line width with lapse of time in Example 1. In the graphs, the symbol □ denotes a data obtained from the reaction system containing a probe, a targeted DNA, and fluorescein with light irradiation; the symbol ■ denotes a data obtained from the reaction system containing a probe, a targeted DNA, and fluorescein without light irradiation; and the symbol ♦ denotes a data obtained from the reaction system containing a probe, and fluorescein with light irradiation, respectively.

FIG. 1A shows the change of the signal intensity ratio with lapse of time, and FIG. 1B shows the change of the ESR signal line width with lapse of time. In the case of the probe alone, the light irradiation caused neither the change of the intensity ratio nor the change of the line width. In the case of fluorescein/probe/M13mp18DNA without light irradiation also, no change was observed in the intensity ratio and the line width.

On the contrary, in the case of fluorescein/probe/ M13mp18DNA with light irradiation (490 nm), the ESR signal intensity ratio was decreased with time. In this case, the ESR signal line width did not change, which shows that the change of the ESR signal intensity ratio was not caused by a chemical change. Thereby, it was confirmed that the spin of the TEMPO disappeared as the result of the charge transfer from fluorescein to TEMPO linked to the probe through the double helix formed from the probe and M13mp18DNA. In other words, a probe-targeted DNA hybrid was detected without B/F separation.

EXAMPLE 2

The same experiment was conducted as in Example 1 except that the base sequence of the probe, SEQ ID NO:2, was as shown below.

5'-GTTGTAAAAGGACGGCCAGT-3'

This sequence in the probe is different from the one in Example 1 in that the tenth base from the 5'-terminal is G instead of C, which means that one base is different from the sequence in Example 1, whereby the probe is mismatched with the M13mp18DNA.

To 0.2 μM of the probe having a mismatched sequence, 0.2 μM of M13mp18DNA was added, and the mixture was annealed in the same manner as in Example 1. Then, after addition of fluorescein, the change of the intensity ratio and the line width of the ESR signal with time were observed.

Consequently, the intensity ratio change was not observed, being different from the result in Example 1, and the intensity was the same as in the case of the probe alone. This means that the mismatched oligonucleotide probe did not form a precise double strand, whereby charge transfer did not occur.

EXAMPLE 3

Synthesis of both-terminal-labeled oligonucleotide probe (5'-TEMPO, 3'-FITC)

(1) Synthesis of 3'-amino-oligonucleotide

A 20-mer oligonucleotide which had a base sequence partially complementary to a single stranded DNA, M13mp18DNA, as the targeted DNA in Example 1 was synthesized on 3'-amino-modifier CPG (1 μmol) made by Gren Research Co. as the support by means of an automatic DNA synthesizing apparatus 381A made by ABI Co. 5'-terminal dimethoxytrityl group was removed on the automatic synthesizing apparatus.

(2) Synthesis of spin-labeled oligonucleotide probe

The nucleotide (1 μmol) synthesized in the above step (1) together with the CGP support thereof was transferred into a gastight syringe. The subsequent reaction was allowed to proceed in this syringe. Onto the CPG support, was added a solution of 50 mg of carbonyl-N,N'-diimidazole (CDI) in 1 ml of dioxane which mixture was left standing at room temperature for one hour. After washing with dioxane, 0.4 ml of 0.2M 4-aminohexylamino-TEMPO solution in DMSO used in Example 1 was added thereto. The solution was left standing at 55° C. for 24 hours, and then washed successively with DMSO, dioxane, and methanol, and dried under a reduced pressure.

The spin-labeled oligonucleotide was separated by aqueous concentrated ammonia, deprotected in a conventional manner, and purified by RPLC in a conventional manner. Thus a spin-labeled oligonucleotide labeled at 5'-terminal with TEMPO was obtained.

(3) Synthesis of a both-terminal-labeled oligonucleotide

The spin-labeled oligonucleotide synthesized in the above step (2) has 3-amino-2-hydroxy group at the 3'-terminal sugar moiety. This amino group was bonded with FITC (fluorescein isothiocyanate, made by Sigma Co.) through the step below.

A solution of 0.2 μmol of the spin-labeled oligonucleotide synthesized in the above step (2) in 700 μl water was mixed with 100 μl of 1M sodium carbonate buffer solution (pH: 9). To the resulting solution, a solution of 2 mg of FITC in DMF was added, and reacted at 35° C. for 24 hours. The reaction mixture was treated by a gel filtration column (NAP-25, made by Pharmacia Co.) to remove a large excess of FITC, and then purified by RPLC to obtain a probe having TEMPO bonded at the 5'-terminal and FITC at the 3'-terminal.

(4) ESR spectrum measurement

Figure 2:
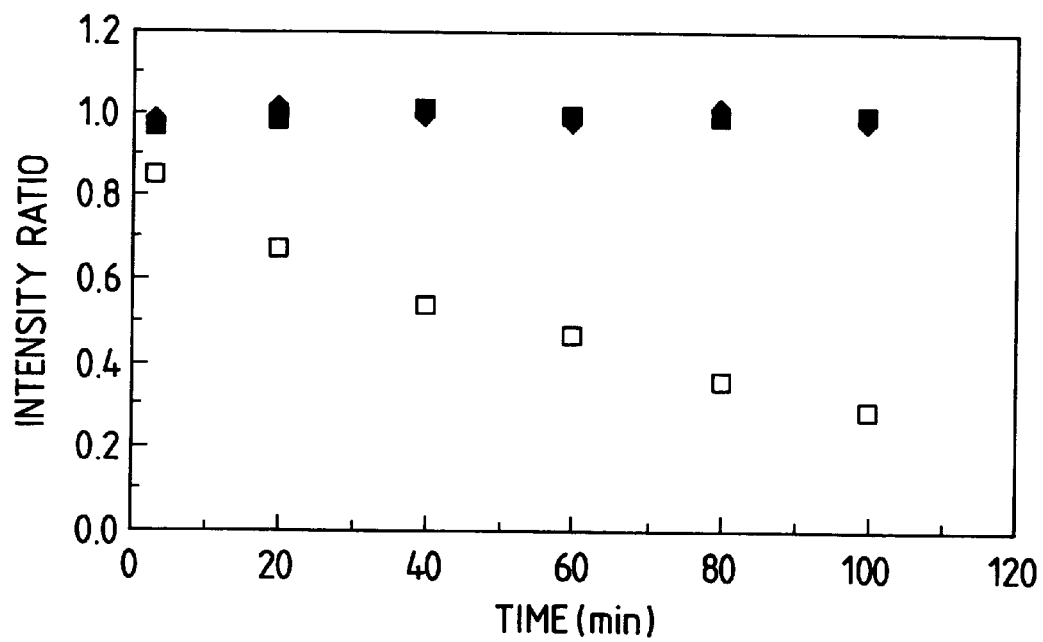
FIG. 2 is a graph showing change of the signal intensity ratio with lapse of time in Example 3. The symbols, □, ■, and ♦, denote the same as in FIGS. 1A and 1B.

The probe and the M13mp18DNA obtained in the above step (3) each in an amount of 0.2 μM were annealed in a conventional manner. Change of the intensity ratio and the line width of the ESR signal were measured in the same manner as in Example 1. The probe alone, and the non-irradiated probe-targeted DNA hybrid did not exhibit change of the intensity ratio, while the probe-targeted DNA hybrid, when irradiated by light of 490 nm which is excitation wavelength of fluorescein, exhibited decrease of the signal with time (see FIG. 2), thereby occurrence of charge transfer being confirmed. Furthermore, the spin disappearance degree was higher than that in Example 1 where fluorescein was not bonded to the probe. Thereby it was confirmed that electron transfer is more effectively conducted when an electron donor is linked to the one terminal and an electron acceptor is linked at the other terminal.

EXAMPLE 4

An oligonucleotide having the same base sequence as that of Example 2 which is different from M13mp18DNA at one base at the middle portion was synthesized, and TEMPO and fluorescein were bonded at the both terminals of the oligonucleotide in the same manner as in Example 3.

The resulting probe and the M13mp18DNA, each in an amount of 0.2 μM, were annealed in a conventional manner. Change of the intensity ratio and the line width of the ESR signal were measured in the same manner as in Example 1. The probe-targeted DNA hybrid, when irradiated with light of excitation wavelength of fluorescein of 490 nm, did not exhibit changes in ESR signal intensity ratio and ESR signal line width like the probe itself and non-irradiated probe-targeted DNA hybrid.

EXAMPLE 5

A 20-mer oligonucleotide having the base sequence as that of Example 1 and having 3'-amino group bonded thereto was synthesized by means of an automatic DNA synthesizing apparatus.

Riboflavine was oxidized to change its —$CH_2OH$ group to a —COOH group. This riboflavine was reacted with the above 3'-amino-oligonucleotide to obtain an oligonucleotide having riboflavine group bonded thereto at the one terminal.

The riboflavine bonded oligonucleotide probe was hybridized with M13mp18 DNA. The reaction medium was a 10 mM phosphate buffer solution. The final concentration of the probe was adjusted to 3 μM, 6 μM, 10 μM, and 20 μM. The final concentration of the M13mp18DNA was adjusted to 10 μM.

The solution of the hybrid of the riboflavine-bonded probe and the M13mp18DNA was irradiated with light of 470 nm, the excitation wavelength of riboflavine, for 5 minutes.

200 μl of the irradiated solution was treated with nuclease $P_1$, and then was digested by E. coli alkaline phosphatase to decompose the probe and the DNA into nucleoside. The decomposition products were separated by HPLC according to the method of Kasai (Gann, 75, p.841–844, (1984)) to quantitatively determine 8-hydroxyguanosine (8-OH-G). The same experiment was conducted with a solution of the riboflavine-bonded probe only, and with a solution of the M13mp18DNA and riboflavine not linked to the probe.

Figure 3:
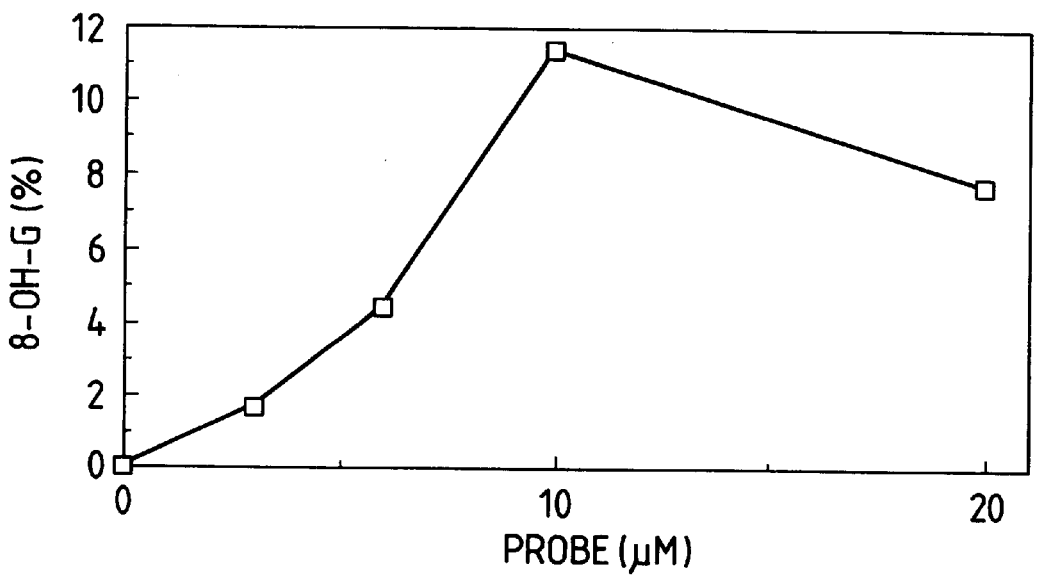
FIG. 3 is a graph showing dependence of the amount of the formed 8-hydroxyguanosine (ratio to G) on the amount of the probe used in Example 5.

As a result, as shown in FIG. 3, formation of 8-OH-G depended on the probe concentration, and the maximum formation was obtained when the ratio of the probe to the targeted DNA was 1:1. No 8-OH-G was detected with a solution of the riboflavine-bonded probe only, and with a solution of the M13mp18DNA and riboflavine not bonded to the probe. Thus, 8-OH-G was formed only when the probe and the DNA were hybridized.

EXAMPLE 6

A riboflavine-bonded 20-mer oligonucleotide was prepared in the same manner as in Example 5. A hybrid was formed between this oligonucleotide as a probe, and M13mp18DNA (as a target DNA). The reaction medium was a 10 mM phosphate buffer solution. The final concentration of the probe was adjusted to 3 μM, 6 μM, 10 μM, and 20 μM. The final concentration of the M13mp18DNA was adjusted to 10 μM. The solution of the hybrid of the riboflavine-bonded probe and the M13mp18DNA was irradiated with light of 470 nm, the excitation wavelength of riboflavine, for 5 minutes.

The same experiments were conducted, as the control, with a solution of the riboflavine-bonded probe only, and with a solution of the M13mp18DNA and riboflavine not bonded to the probe.

Figure 4:
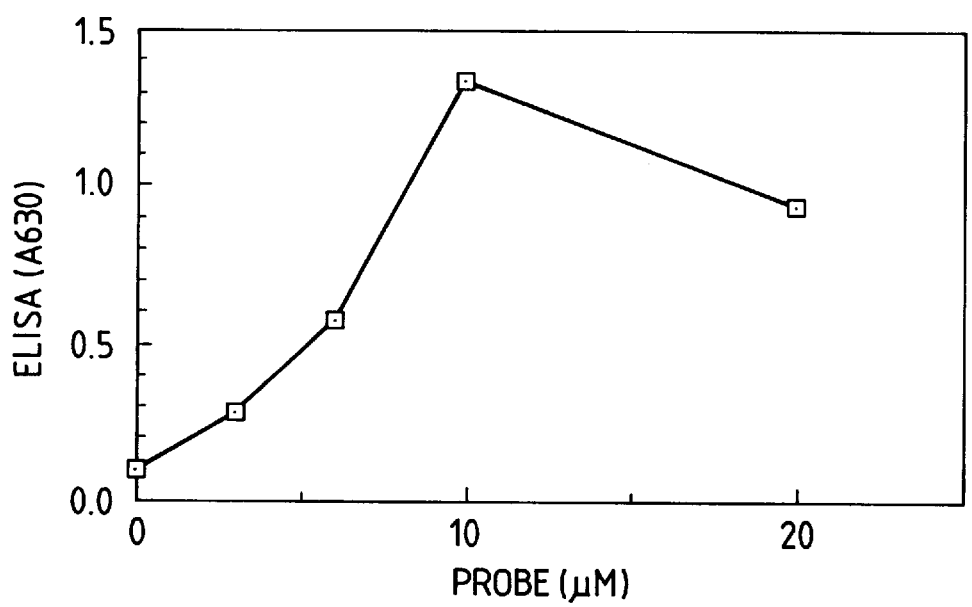
FIG. 4 is a graph showing dependence of the amount of the formed 8-hydroxyguanosine (color reaction by ELISA method) on the amount of the probe used in Example 6.

To each 100 µl of the samples after light irradiation, 50 µg of Salmon Testes DNA was added to fix the sample to a microplate. The sample was reacted with an antibody of 8-OH-G according to an ELISA method. The secondary antibody was quantitatively determined by color development with alkaline phosphatase. The results are shown in FIG. 4. In evaluation with 50 µg of Salmon Testes DNA, the probe/DNA complex developed color corresponding to the probe concentration with maximum color development at the concentration of the probe equimolar to the DNA, while the solution of the riboflavine-bonded probe only and the solution of M13mp18DNA not bonded with the probe and riboflavine developed color as slightly as the Salmon Testes DNA.

EXAMPLE 7

A riboflavine-bonded 20-mer oligonucleotide was prepared in the same manner as in Example 5. A hybrid was formed between this oligonucleotide as a probe, and M13mp18DNA (as a target DNA). The reaction medium was a 10 mM phosphate buffer solution. The final concentration of the probe was adjusted to 3 µM, 6 µM, 10 µM, and 20 µM. The final concentration of the M13mp18DNA was adjusted to 10 µM. The solution of the hybrid of the riboflavine-bonded probe and the M13mp18DNA was irradiated with light of 470 nm, the excitation wavelength of riboflavine, for 5 minutes.

The same experiments were conducted, as the control, with a solution of the riboflavine-bonded probe only, and with a solution of the M13mp18DNA and riboflavine not bonded to the probe.

Figure 5:
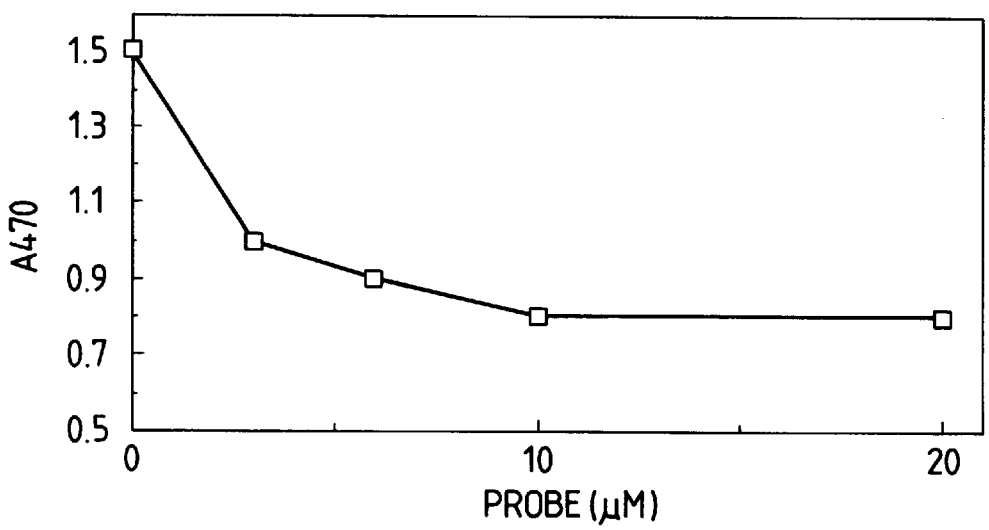
FIG. 5 is a graph showing the interaction of the probe obtained in Example 7 with a hybrid of the targeted DNA.

The light absorbance of the riboflavine was measured at 450 nm for each of the samples. FIG. 5 shows the results. The solution containing only of riboflavine, the solution containing only of riboflavine-bonded probe, and the solution containing M13mp18DNA and riboflavine not bonded to a probe showed a constant optical density of 1.5. On the contrary, the solution containing the hybrid of the probe and M13mp18DNA showed decrease of the light absorbance, which shows that the riboflavine had changed into another substance as the result of charge transfer.

EXAMPLE 8

(1) Formation of succinimide ester of N,N'-dimethyl-2,7-diazapyrene bis(tetrafluoroborate) ($DAP^{2+}$)

$DAP^{2+}$ was synthesized according to the method of Hunig (Ann. Chem. 1973, 339). The purified $DAP^{2+}$ was reacted with succinic anhydride by Friedel-Craft reaction, thereby obtaining a purified product (I) having a carboxyl group. 0.5 g of the purified product (I) was placed in a 100 ml light-resistant reaction vessel, and dissolved in 30 ml of dried DMF. After the solution was cooled to −10° C., 0.4 g of N,N'-succinimidyl carbonate was added thereto. The reaction was allowed to proceed at that temperature for 5 hours. The reaction solution was poured into 150 ml of chloroform. The mixture was washed with 200 ml of aqueous sodium chloride solution three times, and washed with water. The solvent was distilled off. The distillation residue was purified by a silica gel column, and was crystallized from ethanol-isopropanol to obtain $DAP^{2+}$ (II).

(2) Introduction of amino group and thiol group to nucleic acid

A 20-meric oligonucleotide having a base sequence partially complementary to a targeted DNA, M13mp18DNA (single strand), was synthesized by means of an automatic DNA synthesis apparatus (381A, made by ABI Co.). In the synthesis, an amino group was introduced to the 3'-terminal of the oligonucleotide by use of a Fmoc 3'-amino-modifier-CPG column (III) made by Miligene Co. in place of the ordinary amidide reagent CPG. Further after the synthesis, a thiol group was introduced to the 5'-terminal thereof by use of a 5'-hexanol-thiol-linker (III') made by Miligene Co. in place of the ordinary amide reagent.

The oligonucleotide was cut out from the CPG support, deprotected, and purified by high speed liquid chromatography according to a predetermined protocol. The oligonucleotide has the base sequence, SEQ ID NO:1, as below:

5'-GTTGTAAAACGACGGCCAGT-3'

(3) Linking of probe to $DAP^{2+}$

500 µg of the above oligonucleotide having an amino group and a thiol group linked thereto was dissolved in a mixture of 100 µl of 1M sodium carbonate buffer solution (pH: 7.0) and 700 µl of water. Thereto 2 mg of $DAP^{2+}$ (II) dissolved in 200 µl of DMF was added slowly with stirring. The mixture was reacted at 40° C. for 24 hours. After the reaction, the peak of the nucleic acid on the high speed liquid chromatogram disappeared, and a new peak appeared which has absorption of nucleic acid and $DAP^{2+}$ combinedly. The reaction solution was roughly purified by a gel filtration column (NAP-50, made by Pharmacia Co.), and further purified by HPLC. Thereby 450 µg of 3'-$DAP^{2+}$.probe complex (IV) was obtained.

(4) Linking of probe with acridine

400 µg of the probe complex (IV) having a thiol group at the 5'-terminal obtained in the above step (3) was dissolved in a mixture of 100 µl of 1M sodium phosphate buffer solution (pH: 6.0) and 700 µl of water. Thereto, a solution of 1 mg of N-9-acrydinylmaleimide (V, Funakoshi) in 200 µl of DMF was added slowly with stirring. The mixture was reacted at 40° C. for 24 hours. The reaction solution was roughly purified by a gel filtration column, and further purified by high speed liquid chromatography. Thereby 410 µg of 5'-acridine-3'-$DAP^{2+}$.probe complex (VI) was obtained.

(5) Reaction of formation of hybrid of pigment probe and M13mp18DNA 0.2 µM of the probe complex (VI) obtained in the step (4) above and 0.2 µM of M13mp18DNA (made by Takara Shuzo Co., Ltd.) were added to a mixed solution of 1 mM phosphate buffer solution (pH: 7.0)/145 mM NaCl/5 mM KCl, and was heated to 80° C. The mixture was gradually cooled to room temperature to obtain a hybrid of the probe complex(VI) with M13mp18DNA. The absorption spectrum of acridine was shifted toward longer wavelength by about 20 nm as the result of the hybrid formation.

(6) Fluorescence quenching of acridine

Figure 6:
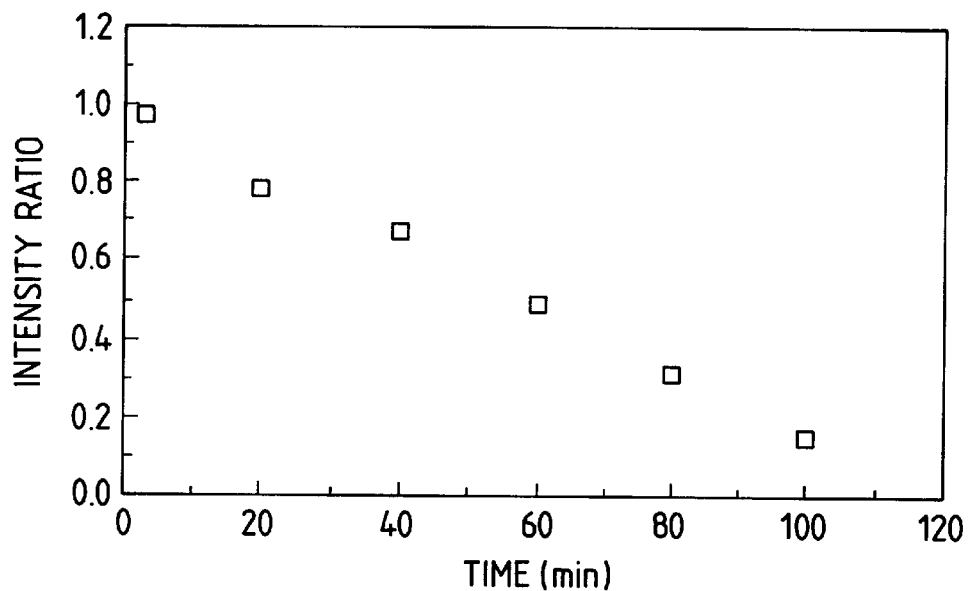
FIG. 6 is a graph showing quenching of fluorescence of acridine obtained in Example 8.

A light irradiation apparatus equipped with a monochrometer was used. The probe and/or the hybrid were irradiated with light of 490 nm, the excitation wavelength of acridine, and the fluorescence at 533 nm was monitored. The probe itself showed slight quenching of fluorescence during long time of irradiation. The fluorescence intensity ratio of the hybrid of the probe complex (VI) with M13mp18DNA was measured relative to the fluorescence strength of the probe itself taken as 1 at each of the irradiation time. The results are shown in FIG. 6.

The fluorescence of the hybrid decreased with the irradiation time. This means that the fluorescence of acridine was quenched as the result of charge transfer from acridine to $DAP^{2+}$ through the aid of the double strand of the probe complex (VI)/M13mp18DNA hybrid. Thus the hybrid of the probe complex (VI)/M13mp18DNA was detected without B/F separation.

(7) Change of absorption spectrum of acridine with lapse of time

Figure 7:
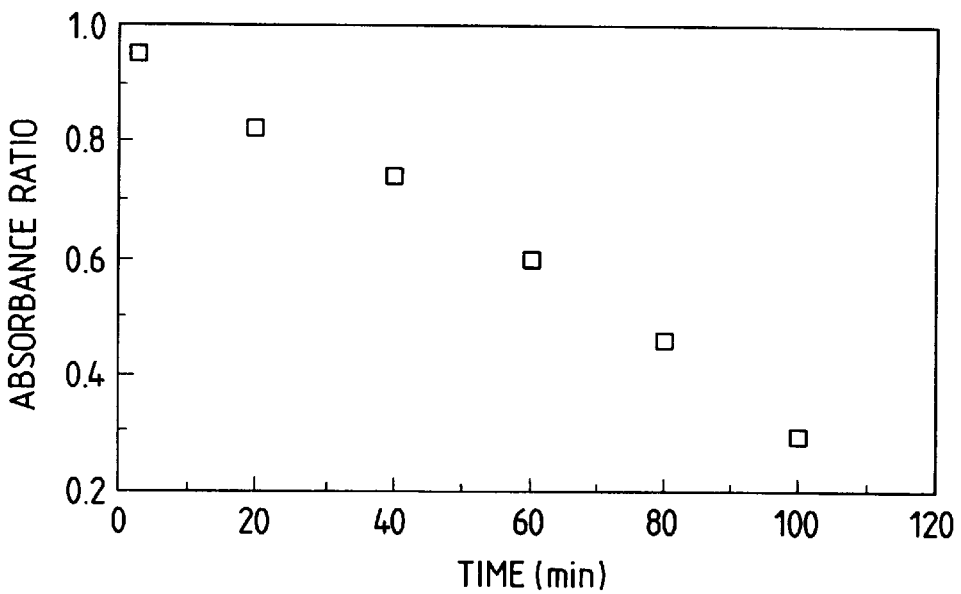
FIG. 7 is a graph showing decrease of absorbance ratio of acridine obtained in Example 8.

The change was observed of the absorption spectrum of the probe complex (VI) itself and the hybrid of probe complex (VI)/M13mp18DNA by continuous irradiation of light of 490 nm with lapse of time. The probe complex (VI) itself showed decrease of the absorbance owing to charge transfer between acridine and $DAP^{2+}$. The absorbance ratio of the hybrid of the probe complex (VI) and M13mp18DNA was measured relative to the absorbance the probe itself taken as 1 at each of the irradiation time. The results are shown in FIG. 7. The absorbance of the hybrid of the probe complex (VI) with M13mp18DNA decreased significantly. This means that the charge transferred from acridine to $DAP^{2+}$ through the stacked base pairs.

EXAMPLE 9

A probe which has acridine at the 5'-terminal and $DAP^{2+}$ at the 3'-terminal linked thereto was prepared in the same manner as in Example 8 except that the oligonucleotide of the base sequence shown below was used as the probe. The resulting probe was reacted with M13mp18DNA, and the fluorescence quenching and decrease of absorbance were measured in the same manner as in Example 8.

5'-GTTGTAAAAGGACGGCCAGT-3'

This base sequence, SEQ ID NO:2, is different from the one in Example 8 in that the tenth base from the 5'-terminal is G instead of C, which means that one sequence is different from the sequence in Example 8 whereby the probe is mismatched with the M13mp18DNA.

As the results, neither the fluorescence quenching nor absorbance decrease was observed with the sample of this Example. Thereby it was confirmed that the charge transfer owing to formation of a hybrid did not occur. This shows that the mismatching of the hybrid was not detected.

The method of detection of a targeted nucleic acid of the present invention has advantages that B/F separation is not necessary. Consequently various operations essential in conventional methods can be omitted such as removal of an excess prove, troublesome treatment for eliminating non-specific adsorption, investigation of operation conditions, and so forth.

The present invention enables selective detection of a hybrid which has precise double helical structure by selecting reagents so that only the signal change of the precise hybrid may be detected, even in the case where mismatching occurs in a reaction system.

What is claimed is:

1. A method for detecting a presence or absence of a nucleic acid hybrid containing a double helical structure formed between a target nucleic acid which may be contained in a sample solution, and a nucleic acid probe having a single-stranded nucleic acid whose base sequence is complementary to that of the target nucleic acid, the method comprising the steps of:

(a) providing a first reagent and a second reagent, the first reagent bound to the single-stranded nucleic acid of the probe and the second reagent in the sample solution, the first and second reagents being capable of interacting with each other by charge transfer through stacks of base pairs constructing the double helical structure of the hybrid;

(b) adding the nucleic acid probe with the first reagent bound thereto to the sample solution, and then putting the sample solution under a condition that the double helical structure is formed when the sample solution contains the target nucleic acid; and (c) detecting a presence or absence of a change in the first or the second reagent caused by the charge transfer to detect the presence or absence of the nucleic acid hybrid, wherein the change caused by the interaction between the reagents is detected chemically.

2. The method according to claim 1, wherein the at least first and second reagents include at least an electron donor and an electron acceptor.

3. The method according to claim 1, wherein at least one of the first and second reagents is an intercalator which is incorporated into the double helical structure.

4. The method according to claim 1, wherein the interaction between the reagents is initiated by light irradiation.

5. The method according to claim 1, wherein the charge transfer is detected by using a third reagent, the third reagent being capable of exhibiting detectable change when the third reagent interacts with the first reagent chemically modified by the charge transfer or the second reagent chemically modified by the charge transfer.

6. A method for detecting a presence or absence of a nucleic acid hybrid containing a complementary double helical structure formed between a target nucleic acid, which may be contained in a sample solution, and a nucleic acid probe comprising the steps of:

(a) providing the nucleic acid probe comprising a reagent and a single-stranded nucleic acid having a complementary base sequence to that of the target nucleic acid, the reagent bound to the single-stranded nucleic acid and the reagent being capable of interacting with the double helical structure by charge transfer;

(b) adding the nucleic acid probe to the sample solution, and then putting the sample solution under a condition that the double helical structure is formed when the sample solution contains the target nucleic acid; and (c) detecting a presence or absence of a change in the first reagent or a nucleoside of which the double helical structure consists, caused by the charge transfer to detect the presence or absence of the nucleic acid hybrid, wherein the charge transfer is detected chemically and occurs through stacks of base pairs forming the double helical structure.

7. The method according to claim 6, wherein the reagent is an intercalator which is incorporated into the double helical structure.

8. The method according to claim 6, wherein the interaction is initiated by light irradiation.

9. A probe for detection of a target nucleic acid, comprising a first reagent and a single-stranded nucleic acid having a complementary base sequence to that of the target nucleic acid, the first reagent being bound to the single-stranded nucleic acid, wherein said first reagent is capable of interacting with a second reagent present with the target nucleic acid in a sample solution by charge transfer through a double helical structure formed by hybridization of the target nucleic acid with the probe, wherein the charge transfer occurs through stacks of base pairs forming the double helical structure, and wherein the first reagent is a pyrylium compound intercalator which is incorporated into the double helical structure and provides a chemically detectable chance when the interacting occurs.

10. The method according to claim 6, wherein the reagent works as an electron donor to cause electron to transfer from the reagent to the double helical structure as an electron acceptor.

11. The method according to claim 6, wherein the double helical structure works as an electron donor to cause electrons to transfer from the double helical structure to the reagent as an electron acceptor.

12. The method according to claim 6, wherein the charge transfer is detected employing a second reagent, the second reagent being capable of exhibiting detectable change when the second reagent interacts with the reagent modified by the charge transfer or a nucleoside of the double helical structure modified by the charge transfer.

13. The method according to claim 12, wherein the interaction between the second reagent and the modified reagent or the modified nucleoside is based on antigen-antibody reaction.

14. The method according to claim 13, wherein the second reagent is an antibody, and the modified reagent or the modified nucleoside is an antigen.

15. A probe for detection of a target nucleic acid comprising a reagent and a single-stranded nucleic acid having a complementary base sequence to that of the target nucleic acid, the reagent being bound to the single-stranded nucleic acid, wherein the reagent is capable of interacting with a double helical structure of a hybrid formed by hybridization of the target nucleic acid with the probe by charge transfer to cause a chemically detectable change of a nucleoside of the double helical structure, wherein the charge transfer occurs through stacks of base pairs forming the double helical structure, and wherein the reagent is an intercalator which is incorporated into the double helical structure and is selected from the group consisting of riboflavin, N,N'-dimethyl-2,7-diazapyrene, Rose Bengal, Floxin B, eosin, methylene blue and Safranine T.

16. A probe for detection of a target nucleic acid comprising a first reagent, a second reagent and a single-stranded nucleic acid having a complementary base sequence to that of the target nucleic acid, the first reagent and the second reagent being linked to the single-stranded nucleic acid of the probe, and the first reagent and the second reagent being capable of interacting with each other by charge transfer through the double helical structure of a hybrid formed by hybridization of the target nucleic acid with the probe, wherein one of the first and second reagents is a spin-labeling agent which causes change in electron spin resonance spectrum on accepting an electron, the spin-labeling agent being selected from the group consisting of 4,4-dimethyloxazolidine-N-oxyl, 2,2,5,5-tetramethylpyrrolidine-N-oxyl and 2,2,6,6-tetramethylpiperidine-N-oxyl, and the other reagent is a substance which works as an electron donor.

17. The probe according to claim 16, wherein the first reagent is an electron donor, and the second reagent is an electron acceptor.

18. The probe according to claim 16, wherein at least one of the first reagent and the second reagent is an intercalator which is incorporated into the double helical structure.

19. The probe according to claim 16, wherein the first reagent is to the single terminal portion of the single-stranded nucleic acid, and the second reagent is linked to the other terminal portion of the single-stranded nucleic acid.

20. The probe according to claim 16, wherein at least one of the first reagent and the second reagent is a pigment.

21. The probe according to claim 16, wherein the first reagent is a substance which causes chemically detectable change in the first reagent or the second reagent.

22. The probe according to claim 16, wherein the first reagent is a substance which causes emergence of a new absorption spectrum when the first reagent interacts with the second reagent by the charge transfer.

23. The probe according to claim 16, wherein at least one of the first reagent and the second reagent is a substance capable of interacting with a third reagent when the first and the second reagents interact with each other by the charge transfer, and the third reagent being capable of exhibiting detectable change when the third reagent interacts with the first reagent chemically modified by the charge transfer or the second reagent chemically modified by the charge transfer.

24. The probe according to claim 16, wherein the substance which works as an electron donor is selected from the group consisting of acridine, anthracene, pyrene, ethidium bromide, pyrylium, proflavine, porphyrin, thiazole orange dimer, oxazole yellow, 4',6-diamino-2-phenylindole dihydrochloride, propidium iodide, cyanine, azulene, three-nucleus pigment, dansyl, fluorescein, eosin, rhodamine and riboflavine.

25. The probe according to claim 16, wherein the spin-labeling agent is 2,2,6,6-tetramethylpiperdine-N-oxyl, and the other reagent is fluorescein isothiocyanate.

26. A method, of detecting a presence or absence of a nucleic acid hybrid containing a complementary double helical structure formed between a target nucleic acid which may be contained in a sample solution, and a nucleic acid probe comprising the steps of:

(a) providing the nucleic acid probe comprising a first reagent, a second reagent, and a single-stranded nucleic acid having a complementary base sequence to that of the target nucleic acid, the first reagent and the second reagent being linked to the single-stranded nucleic acid of the probe, and the first reagent and the second reagent being capable of interacting with each other by charge transfer through the double helical structure of the hybrid;

(b) adding the probe to the sample solution, and then putting the sample solution under a condition that the double helical structure is formed when the sample solution contains the target nucleic acid; and (c) detecting a presence or absence of a change in the first reagent or the second reagent caused by the charge transfer between the reagents through a double helical structure of the hybrid to detect the presence or absence of the nucleic acid hybrid, wherein the charge transfer occurs through stacks of base pairs forming the double helical structure and wherein the charge transfer is detected chemically.

27. A method, of detecting a presence or absence of a nucleic acid hybrid containing a complementary double helical structure formed between a target nucleic acid which may be contained in a sample solution, and a nucleic acid probe comprising the steps of:

(a) providing the nucleic acid probe comprising a first reagent, a second reagent, and a single-stranded nucleic acid having a complementary base sequence to that of the target nucleic acid, the first reagent and the second reagent being linked to the single-stranded nucleic acid of the probe, and the first reagent and the second reagent being capable of interacting with each other by charge transfer through the double helical structure of the hybrid;

(b) adding the probe to the sample solution, and then putting the sample solution under a condition that the double helical structure is formed when the sample solution contains the target nucleic acid; and (c) detecting a presence or absence of a change in the first reagent or the second reagent caused by the charge transfer between the reagents through a double helical structure of the hybrid to detect the presence or absence of the nucleic acid hybrid, wherein the charge transfer occurs through stacks of base pairs forming the double helical structure, wherein the charge transfer is detected by using a third reagent, the third reagent being capable of exhibiting detectable change when the third reagent interacts with the first reagent chemically modified by the charge transfer or the second reagent chemically modified by the charge transfer.

28. The method according to claim 26 or 27, wherein at least one of the first reagent and the second reagent is an intercalator which is incorporated into the double helical structure.

29. The method according to claim 26 or 27, wherein the first reagent is liked to one terminal portion of the probe, and a second reagent is linked to the other terminal portion of the probe.

30. The method according to claim 26 or 27, wherein the first reagent is an electron donor and the second reagent is an electron acceptor.

31. The method according to claim 26 or 27, wherein at least one of the first reagent and the second reagent is a pigment.

32. The method according to claim 26 or claim 27, wherein the charge transfer is initiated by light irradiation.

33. The method according to claim 26 or 27, wherein at least one of the first reagent and the second reagent is an intercalator incorporated into the double helical structure.

34. A process for producing a probe having a first reagent and a second reagent both of which are capable of interacting with each other by charge transfer when the probe complementary hybridizes with a target nucleic acid in a sample comprising the steps of:

(a) providing a desired length of a single stranded nucleic acid capable of complementary hybridizing with the target nucleic acid;

(b) introducing an amino group and a thiol group into 3'-terminal and 5'-terminal of the nucleic acid respectively;

(c) reacting N,N'-dimethyl-2,7-diazapyrene bis (tetrafluoroborate) with the amino group at the 3'-position of the nucleic acid; and (d) reacting acridine with the thiol group at the 5'-position of the nucleic acid.

35. A method for detecting a presence or absence of a nucleic acid hybrid containing a double helical structure formed between a target nucleic acid which may be contained in a sample solution, and a nucleic acid probe having a single-stranded nucleic acid whose base sequence is complementary to that of the target nucleic acid, the method comprising the steps of:

(a) providing at least a first reagent and a second reagent, the first reagent bound to the single-stranded nucleic acid of the probe and the second reagent in the sample solution, the first and second reagents being capable of interacting with each other by charge transfer through the double helical structure of the hybrid;

(b) adding the nucleic acid probe with the first reagent bound thereto to the sample solution, and then putting the sample solution under a condition that the double helical structure is formed when the sample solution contains the target nucleic acid; and (c) detecting a presence or absence of a change in the first reagent or the second reagent caused by the charge transfer between the reagents through a double helical structure of the hybrid to detect the presence or absence of a nucleic acid hybrid, wherein the change in at least one of the first reagent and the second reagents caused by the charge transfer between the first and the second reagents is detected optically, and wherein the charge transfer is detected by spectrum change in ESR employing a spin-labeling agent.

36. A method for detecting a presence or absence of a nucleic acid hybrid containing a double helical structure formed between a target nucleic acid which may be contained in a sample solution, and a nucleic acid probe having a single-stranded nucleic acid whose base sequence is complementary to that of the target nucleic acid, the method comprising the steps of:

(a) providing at least a first reagent and a second reagent, the first reagent bound to the single-stranded nucleic acid of the probe and the second reagent in the sample solution, the first and second reagents being capable of interacting with each other by charge transfer through the double helical structure of the hybrid;

(b) adding the nucleic acid probe with the first reagent bound thereto to the sample solution, and then putting the solution under a condition that the double helical structure is formed when the sample solution contains the target nucleic acid; and (c) detecting a presence or absence of a change in the first reagent or the second reagent caused by the charge transfer between the reagents through a double helical structure of the hybrid to detect the presence or absence of a nucleic acid hybrid, wherein the change caused by the interaction between the reagents is detected chemically, and wherein the charge transfer is detected by using a third reagent, the third reagent being capable of exhibiting detectable change when the third reagent interacts with the first reagent chemically modified by the charge transfer or the second reagent chemically modified by the charge transfer based on antigen-antibody reaction.

37. The method according to claim 36, wherein the third reagent is an antigen, and the chemically modified first reagent or the chemically modified second reagent is an antibody.

38. A method for detecting a presence or absence of a nucleic acid hybrid containing a double helical structure formed between a target nucleic acid which may be contained in a sample solution, and a nucleic acid probe having a single-stranded nucleic acid whose base sequence is complementary to that of the target nucleic acid, the method comprising the steps of:

(a) providing at least a first reagent and a second reagent, the first reagent bound to the single-stranded nucleic acid of the probe and the second reagent in the sample solution, the first and second reagents being capable of interacting with each other by charge transfer through stacks of base pairs constructing the double helical structure of the hybrid;

(b) adding the nucleic acid probe with the first reagent bound thereto to the sample solution, and then putting the sample solution under a condition that the double helical structure is formed when the sample solution contains the target nucleic acid; and (c) detecting a presence or absence of a change in the first reagent or the second reagent caused by the charge transfer between the reagents through a double helical structure of the hybrid to detect the presence or absence of a nucleic acid hybrid, wherein at least one of the reagents is a pyrylium compound.

39. A method for detecting a presence or absence of a nucleic acid hybrid containing a complementary double helical structure formed between a target nucleic acid which may be contained in a sample solution, and a nucleic acid probe, the method comprising the steps of:

(a) providing the nucleic acid probe comprising a reagent and a single-stranded nucleic acid having a complementary base sequence to that of the target nucleic acid, the reagent bound to the single-stranded nucleic acid of the nucleic acid probe, and the reagent being capable of interacting with the double helical structure by charge transfer;

(b) adding the nucleic acid probe to the sample solution, and then putting the sample solution under a condition that the double helical structure is formed when the sample solution contains the target nucleic acid; and (c) detecting a presence or absence of a change in the reagent or a nucleoside of which the double helical structure consists, caused by the charge transfer to detect the presence or absence of the nucleic acid hybrid, wherein the double helical structure works as an electron donor to cause electrons to transfer from the double helical structure to the reagent as an electron acceptor, and wherein the change caused by the charge transfer is detected optically by spectrum change in ESR employing a spin-labeling agent as the reagent.

40. A method for detecting a presence or absence of a nucleic acid hybrid containing a complementary double helical structure formed between a target nucleic acid which may be contained in a sample solution, and a nucleic acid probe, the method comprising the steps of:

(a) providing the nucleic acid probe comprising a reagent and a single-stranded nucleic acid having a complementary base sequence to that of the target nucleic acid, the reagent bound to the single-stranded nucleic acid of the nucleic acid probe, and the reagent being capable of interacting with the double helical structure by charge transfer;

(b) adding the nucleic acid probe to the sample solution, and then putting the sample solution under a condition that the double helical structure is formed when the sample solution contains the target nucleic acid; and (c) detecting a presence or absence of a change in the reagent or a nucleoside of which the double helical structure consists, caused by the charge transfer to detect the presence or absence of the double helical structure, wherein the change caused by the charge transfer is detected by identifying a nucleoside modified by the charge transfer employing a chromatogram.

41. A method of detecting a presence or absence of a nucleic acid hybrid containing a complementary double helical structure formed between a target nucleic acid which may be contained in a sample solution, and a nucleic acid probe, the method comprising the steps of:

(a) providing the nucleic acid probe comprising a first reagent, a second reagent and a single-stranded nucleic acid having a complementary base sequence to that of the target nucleic acid, the first reagent and the second reagent being linked to the single-stranded nucleic acid of the probe, and the first reagent and the second reagent being capable of interacting with each other by charge transfer through the double helical structure of the hybrid;

(b) adding the probe to the sample solution, and then putting the sample solution under a condition that the double helical structure is formed when the sample solution contains the target nucleic acid; and (c) detecting a presence or absence of a change in the first reagent or the second reagent caused by the charge transfer between the reagents through a double helical structure of the hybrid to detect the presence or absence of the nucleic acid hybrid, wherein at least one of the first reagent and the second reagent is a pyrylium compound.

42. A method of detecting a presence or absence of a nucleic acid hybrid containing a complementary double helical structure formed between a target nucleic acid which may be contained in a sample solution, and a nucleic acid probe, the method comprising the steps of:

(a) providing the nucleic acid probe comprising a first reagent, a second reagent and a single-stranded nucleic acid having a complementary base sequence to that of the target nucleic acid, the first reagent and the second reagent being linked to the single-stranded nucleic acid of the probe, and the first reagent and the second reagent being capable of interacting with each other by charge transfer through the double helical structure of the hybrid;

(b) adding the probe to the sample solution, and then putting the sample solution under a condition that the double helical structure is formed when the sample solution contains the target nucleic acid; and (c) detecting a presence or absence of a change in the first reagent or the second reagent caused by the charge transfer between the reagents through a double helical structure of the hybrid to detect the presence or absence of the nucleic acid hybrid, wherein the first reagent is an electron donor and the second reagent is an electron acceptor, wherein the change caused by the charge transfer is detected optically by spectrum change in ESR employing a spin-labeling agent as the electron acceptor.

43. A method of detecting a presence or absence of a nucleic acid hybrid containing a complementary double helical structure formed between a target nucleic acid which may be contained in a sample solution, and a nucleic acid probe, the method comprising the steps of:

(a) providing the nucleic acid probe comprising a first reagent, a second reagent and a single-stranded nucleic acid having a complementary base sequence to that of the target nucleic acid, the first reagent and the second reagent being linked to the probe, and the first reagent and the second reagent being capable of interacting with each other by charge transfer through the double helical structure of the hybrid;

(b) adding the probe to the sample solution, and then putting the sample solution under a condition that the double helical structure is formed when the sample solution contains the target nucleic acid; and (c) detecting a presence or absence of a change in the first reagent or the second reagent caused by the charge transfer between the reagents through a double helical structure of the hybrid to detect the presence or absence of the nucleic acid hybrid, wherein the chance caused by the charge transfer is detected by using a third reagent, the third reagent being capable of exhibiting detectable change when the third reagent interacts with the first reagent chemically modified by the charge transfer or the second reagent chemically modified by the charge transfer and wherein the interaction between the third reagent and the chemically modified first reagent or the chemically modified second reagent is based on antigen-antibody reaction.

44. The method according to claim 43, wherein the third reagent is an antigen, and the chemically modified first reagent or the chemically modified second reagent is an antibody.

45. A probe for detection of a target nucleic acid comprising a first reagent, a second reagent and a single-stranded nucleic acid having a complementary base sequence to that of the target nucleic acid, the first reagent and the second reagent being linked to the single-stranded nucleic acid of the probe, and the first reagent and the second reagent being capable of interacting with each other by charge transfer through the double helical structure of a hybrid formed by hybridization of the target nucleic acid with the probe, wherein at least one of the first reagent and the second reagent is a pyrylium compound.

46. A method for ascertaining a presence or absence of a mismatch in a nucleic acid hybrid containing a double helical structure formed between a nucleic acid probe and a target nucleic acid in a sample solution comprising the steps of:

(a) providing the nucleic acid probe comprising a first reagent, a second reagent and a single-stranded nucleic acid which is likely to be complementary to a base sequence of the target nucleic acid, the first reagent and the second reagent being linked to the single-stranded nucleic acid of the nucleic acid probe, and the first reagent and the second reagent being capable of interacting with each other by charge transfer through stacks of base pairs constructing the double helical structure of the hybrid, the charge transfer occurring when the double helical structure is free from any mismatches between the reagents;

(b) adding the nucleic acid probe with the first and second reagents bound thereto to the sample solution which contains the target nucleic acid, and then putting the sample solution under a condition that the double helical structure is formed;

(c) detecting a presence or absence of a change in the first reagent or the second reagent caused by the transfer between the reagents; and (d) ascertaining the presence or absence of a mismatch in the hybrid by the result of the step (c), wherein the step (c) includes detecting the electron transfer between the reagents chemically.

47. A method for ascertaining a presence or absence of a mismatch in a nucleic acid hybrid containing a double helical structure formed between a nucleic acid probe and a target nucleic acid in a sample solution comprising the steps of:

(a) providing the nucleic acid probe comprising a first reagent, a second reagent and a single-stranded nucleic acid which is likely to be complementary to a base sequence of the target nucleic acid, the first reagent and the second reagent being linked to the single-stranded nucleic acid of the nucleic acid probe, and the first reagent and the second reagent being capable of interacting with each other by charge transfer through stacks of base pairs constructing the double helical structure of the hybrid, the charge transfer occurring when the double helical structure is free from any mismatches between the reagents;

(b) adding the nucleic acid probe with the first and second reagents bound thereto to the sample solution which contains the target nucleic acid, and then putting the sample solution under a condition that the double helical structure is formed;

(c) detecting a presence or absence of a change in the first reagent or the second reagent caused by the transfer between the reagents; and (d) ascertaining the presence or absence of a mismatch in the hybrid by the result of the step (c), wherein the step (c) includes detecting the electron transfer between the reagents by spectrum change in ESR employing a spin-labeling agent as the first or the second reagent.

* * * * *

UNITED STATES PATENT AND TRADEMARK OFFICE
CERTIFICATE OF CORRECTION

PATENT NO.  : 5,939,256
DATED       : August 17, 1999
INVENTOR(S) : NOBUKO YAMAMOTO ET AL.

It is certified that error appears in the above-identified patent and that said Letters Patent is hereby corrected as shown below:

Title page,
AT [56] REFERENCES CITED

OTHER PUBLICATIONS

"(1956) Balban," should read --(1956) ¶ Balban,--.

COLUMN 1

Line 34, "of effective" should read --of the effective--; and
Line 45, "being" should read --beings--.

COLUMN 2

Line 11, "with an" should read --with a--; and
Line 63, "corresponding that" should read --corresponding to that--.

COLUMN 4

Line 1, "steps adding" should read --steps of adding--; and
Line 34, "still further" should read --still a further--.

COLUMN 5

Line 49, "base" should read --bases--.

UNITED STATES PATENT AND TRADEMARK OFFICE
CERTIFICATE OF CORRECTION

PATENT NO.    : 5,939,256

DATED         : August 17, 1999

INVENTOR(S)   : NOBUKO YAMAMOTO ET AL.

It is certified that error appears in the above-identified patent and that said Letters Patent is hereby corrected as shown below:

COLUMN 7

Line 7, "does not be" should read --is not--; and
Line 51, "according its" should read --according to its--.

COLUMN 8

Line 6, "withdrawns" should read --withdrawn--;
Line 7, "withdraw" should read --withdrawn--; and
Line 42, "spread of" should read --spread--.

COLUMN 9

Line 67, "Å more" should read --Å, more--.

COLUMN 10

Line 10, "be in" should be deleted.

COLUMN 12

Line 13, "interval" should read --intervals--.

COLUMN 15

Line 37, "containing" should read --consisting--; and
Line 38, "containing" should read --consisting--.

UNITED STATES PATENT AND TRADEMARK OFFICE
CERTIFICATE OF CORRECTION

PATENT NO.    : 5,939,256
DATED         : August 17, 1999
INVENTOR(S)   : NOBUKO YAMAMOTO ET AL.

It is certified that error appears in the above-identified patent and that said Letters Patent is hereby corrected as shown below:

COLUMN 16

Line 6, "amidide" should read --amide--.

COLUMN 19

Line 66, "chance" should read --change--.

COLUMN 20

Line 63, "is to the single" should read --is linked to one--.

COLUMN 21

Line 27, "method," should read --method--; and
Line 54, "method," should read --method--.

COLUMN 22

Line 22, "liked" should read --linked--.

COLUMN 23

Line 8, "reagents" should read --reagent--.

UNITED STATES PATENT AND TRADEMARK OFFICE
CERTIFICATE OF CORRECTION

PATENT NO. : 5,939,256

DATED : August 17, 1999

INVENTOR(S) : NOBUKO YAMAMOTO ET AL.

It is certified that error appears in the above-identified patent and that said Letters Patent is hereby corrected as shown below:

COLUMN 25

Line 67, "chance" should read --change--.

Signed and Sealed this

Twenty-second Day of August, 2000

Attest:

Q. TODD DICKINSON

*Attesting Officer*    *Director of Patents and Trademarks*

```
                          SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:1:

GTTGTAAAAC GACGGCCAGT                                                      20

(2) INFORMATION FOR SEQ ID NO:2:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:2:

GTTGTAAAAG GACGGCCAGT                                                      20
```